(12) United States Patent
Periana

(10) Patent No.: US 7,368,598 B2
(45) Date of Patent: May 6, 2008

(54) PROCESS FOR CONVERTING METHANE TO ACETIC ACID

(75) Inventor: Roy A. Periana, Marina Del Rey, CA (US)

(73) Assignee: University of South California, Los Angeles, CA (US)

( * ) Notice: Subject to any disclaimer, the term of this patent is extended or adjusted under 35 U.S.C. 154(b) by 133 days.

(21) Appl. No.: 11/186,077

(22) Filed: Jul. 19, 2005

(65) Prior Publication Data

US 2006/0167314 A1    Jul. 27, 2006

Related U.S. Application Data

(60) Provisional application No. 60/589,344, filed on Jul. 19, 2004.

(51) Int. Cl.
*C07C 51/16* (2006.01)
*C07C 51/215* (2006.01)
*C07C 51/285* (2006.01)
*C07C 51/295* (2006.01)
*C07C 51/305* (2006.01)

(52) U.S. Cl. ..................... 562/542; 562/607

(58) Field of Classification Search ................. 562/542
See application file for complete search history.

(56) References Cited

U.S. PATENT DOCUMENTS 5,510,525 A * 4/1996 Sen et al. .................... 562/542
5,659,077 A * 8/1997 McFarlan ................. 562/512.2
7,009,074 B2 * 3/2006 Zerella et al. .............. 562/522

OTHER PUBLICATIONS

Database CAPLUS on STN, Acc. No. 1995:427482, Kurioka et al., Chemistry Letters (1995), 3, p. 244 (abstract).*
Database CAPLUS on STN, Acc. No. 2001:194152, Chepaikin et al., Journal of Molecular Catalysis A: Chemical (2001), 169(1-2), p. 89-98 (abstract).*
Linke, D., et al., "Catalytic Partial Oxidation of Ethane to Acetic Acid over $Mo_1V_{0.25}Nb_{0.12}Pd_{0.0005}O_x$", *Chem. Commun.*, pp. 1885-1886 (1998).
Nizova, G., et al., "Carboxylation of Methane with Co or $Co_2$ in Aqueous Solution Catalysed by Vanadium Complexes", *Chem. Commun.*, pp. 1885-1886, (1998).
Periana, R., et al., "A Mercury-Catalyzed, High-Yield System for the Oxidation of Methane to Methanol", *Science*, 259(5093):340-343, Jan. 1993.
Periana, R., et al., "Catalytic, Oxidative Condensation of $CH_4$ to $CH_3COOH$ in One Step via CH Activation", *Science*, 301(5634):814-818, Aug. 2003.
Periana, R., et al., "High yield conversion of methane to methyl bisulfate catalyzed by iodine cations", *Chem. Commun.*, pp. 2376-2377, (2002).
Periana, R., et al., "Platinum Catalysts for the High-Yield Oxidation of Methane to a Methanol Derivative", *Science*, 280(5363):560-564, Apr. 1998.
Sen, A., "Catalytic Functionalization of Carbon-Hydrogen and Carbon—Carbon Bonds in Protic Media", *Accounts of Chemical Research*, 31(9):550-557, 1998.
Shibamoto, A., et al., "Aerobic oxidation of ethane to acetic acid catalyzed by N,N'-dihydroxypyromellitimide combined with Co species", *Tetrahedron Letters*, 43(49):8859-8861, Dec. 2002.

* cited by examiner

*Primary Examiner*—Brian Davis
(74) *Attorney, Agent, or Firm*—Fish & Richardson P.C.

(57) ABSTRACT

Provided herein are processes for conversion of methane to acetic acid. In one embodiment, the processes are for direct, selective conversion of methane to acetic acid in a single step.

20 Claims, 2 Drawing Sheets

PROCESS FOR CONVERTING METHANE TO ACETIC ACID

This application claims the benefit of priority under 35 U.S.C. §119(e) to U.S. provisional application Ser. No. 60/589,344, entitled "A Process For Converting Methane To Acetic Acid" to Periana et al., filed Jul. 19, 2004. The contents of the provisional application are incorporated by reference herein.

FIELD

Provided herein are processes for conversion of methane to acetic acid. In one embodiment, the processes are for direct, selective conversion of methane to acetic acid in single step.

BACKGROUND

Natural gas is abundantly available and provides a power source as a combustible fuel. However, the use of natural gas as fuel is often inconvenient for reasons of storage and handling. Accordingly, it would be desirable to convert components of natural gas to more valuable hydrocarbons. For example, conversion of natural gas to a liquid fuel would obviate certain problems of storage and handling. The main component of natural gas is methane. An efficient technology to economically convert methane directly to useful products, including acetic acid is desirable. The direct, selective conversion of methane to useful products is challenging because the C—H bonds of methane are strong, and efficient catalysts that can economically, selectively, and directly convert methane to functionalized molecules are needed.

Available methods for conversion of methane to acetic acid include a three-step process based on the high-temperature conversion of methane to syn-gas, conversion of syn-gas to methanol and finally carbonylation of the methanol to acetic acid. This process is capital and energy-intensive.

Therefore, there is a continuing need for a method for direct, selective conversion of methane to acetic acid.

SUMMARY

Provided herein are processes for directly converting methane to acetic acid. In certain embodiments, both carbons of acetic acid are obtained from methane. In such embodiments, no additional sources of carbon are required: both carbons are obtained directly by in-situ oxidation. In other embodiments, the process involves adding CO, $H_2CO$, $HCO_2H$ or methanol as a source of carbon for the carboxylic group. This reaction is less exothermic and can be easier to control and the process costs may be less.

The processes provided herein can be catalyzed by a platinum group metal based catalyst. The processes can be carried out in presence of any oxidant that can oxidize platinum group metal rapidly. Examples of oxidants include, but are not limited to $H_2SO_4$, $O_2$, $H_2SeO_4$, $TeO_3$, $H_2O_2$, trifluoroacetic, triflic acid and ionic liquids. In certain embodiments, a co-catalyst that facilitates the oxidation can be added. Acetic acid and water formed in the reaction can be removed by distillation.

DETAILED DESCRIPTION

Provided herein are processes for direct conversion of methane to acetic acid. In certain embodiments, the processes provided herein are for directly converting methane to acetic acid in presence of a platinum group metal based catalyst and an oxidant. The platinum group metal based catalyst used in the processes can be Platinum, Palladium, Rhodium, Ruthenium, Osmium or Iridium based catalyst. In certain embodiments, the reaction is catalyzed by a Pd (II) catalyst, such as $Pd(OAc)_2$, $PdSO_4$, $Pd(NO_3)_2$, or $PdCl_2$. In certain embodiments, the catalyst is $PdSO_4$. The reaction, in certain embodiments, can be represented as:

Scheme I

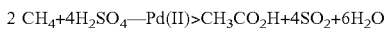

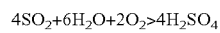

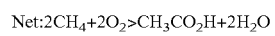

The direct, oxidative condensation of methane to acetic acid in acidic solution is formally an eight-electron oxidation process, and most likely involves several reaction intermediates. The combined selectivity of the reaction for methanol and acetic acid is >90%.

Without being bound to any particular theory, it is proposed that there is both a facile pathway for the formation of acetic acid as well as a mechanism that minimizes decomposition. This is consistent with the observation that addition of $O_2$ (known to react rapidly with free-radicals and a test for the involvement of radicals) has no effect on the reaction rate or selectivity. Acetic acid is more stable than methanol in hot sulfuric acid and is resistant to over oxidation even in the presence of catalysts. The reaction is Pd(II) catalyzed. No products are formed in the absence of added Pd(II) and the reaction rate depends on both the methane pressure and the concentration of Pd(II).

The reaction represented by scheme I has high selectivity, combined selectivity for methanol and acetic acid formation being about 90% over the course of the reaction. The conversion can be done in a single step. In certain embodiments, the selectivity for methanol and acetic acid formation is between 70-95% over the course of the reaction. The conversion can be done in a single step. In certain embodiments, the selectivity for methanol and acetic acid formation is about 70%, 75%, 80% or 85% over the course of the reaction. The selectivities for the formation methanol and acetic acid in the reaction represented by scheme I are time dependent, with higher selectivity for methanol at shorter reaction times and for acetic acid with higher reaction times (Example 1, FIG. 1 and Table 1). The reactions can be reproduced, in certain embodiments, with 10-15% accuracy.

Acetic acid and water formed during the reaction can be removed by suitable means, such as distillation. Pd metal formed in the reaction can contribute to the slowing and eventually stopping the reaction because the Pd metal can not be re-dissolved with hot sulfuric acid.

Reaction Mechanism for the Reaction of Scheme I

Figure 2:
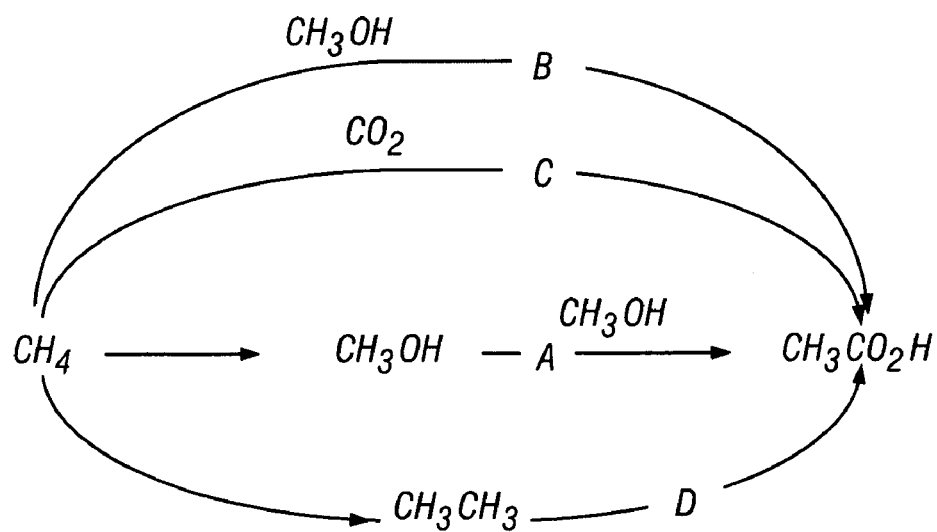
FIG. 2 is a schematic representation of possible pathways for C—C Bond formation of Acetic Acid from Methane.

Some possible pathways that are considered for the reaction represented by scheme I are shown in FIG. 2. Based on the observation that the selectivities for methanol and acetic acid are time dependent, methanol is likely an intermediate to acetic acid. Two fundamentally different pathways that involve methanol as an intermediate are possible. In pathway A, two methanol molecules oxidatively condense. In this case, both carbons of acetic acid are derived from the methanol. Such a process could occur via a methanol carbonylation reaction with some "CO" source (either free CO, other reactive carbon, species formed at low steady state concentrations below level of detection or other species such as Pd—CO-complexes) being generated from the in situ oxidation of methanol by sulfuric acid. Pathway B is fundamentally different and involves the oxidative condensation of methane and methanol generated in situ from methane. In this case, one carbon of acetic acid can be derived directly from methane and the other from methanol. Such a process can involve the reaction of Pd—$CH_3$ species, generated from electrophilic C—H activation of methane by Pd(II), with "CO" to generate Pd—$COCH_3$ species that produces acetic acid. Two other less likely pathways are C and D. Pathway C is considered as $CO_2$ is observed as a product and the coupling of $CO_2$ and $CH_4$ is reported (Nizova et al. Chem. Commun. 1998, 1885). Pathway D is considered even though ethane or other hydrocarbon products are not observed, such species could be formed at low steady state concentrations and both the oxidative coupling of methane to ethane (or other C2 products) and the oxidation of ethane to acetic acid are known reactions.

Figure 3:
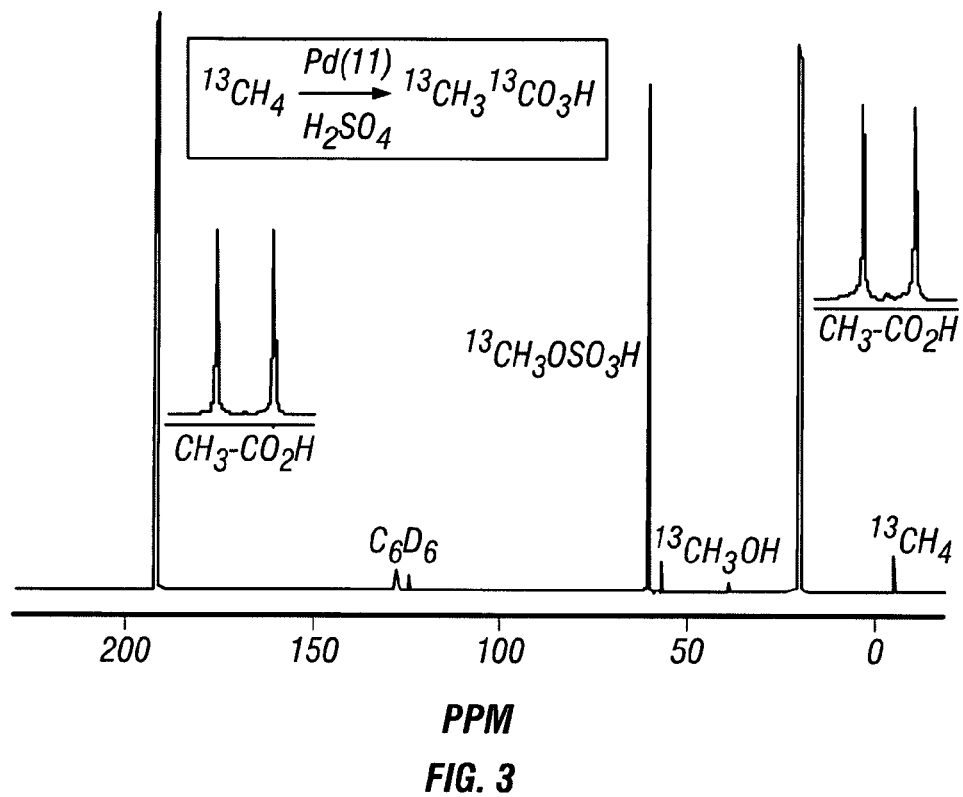
FIG. 3 is $^{13}C$ NMR of reaction mixture starting with $^{13}CH_4$.

Pathway C can be ruled out based on the unfavorable thermodynamics for $CH_4/CO_2$ coupling reactions with $^{13}CH_4/^{12}CO_2$ mixtures (~10:1 molar ratio, 98% $^{13}C$ enrichment). Thus, while acetic acid is formed in this reaction, the diagnostic doublet pattern in the $^{13}C$-NMR (FIG. 3) that are observed for both the $CH_3$— and —$CO_2$ groups of acetic acid show that only $^{13}CH_3^{13}CO_2H$ is formed, showing that both carbons originate from $^{13}CH_4$.

Figure 4:
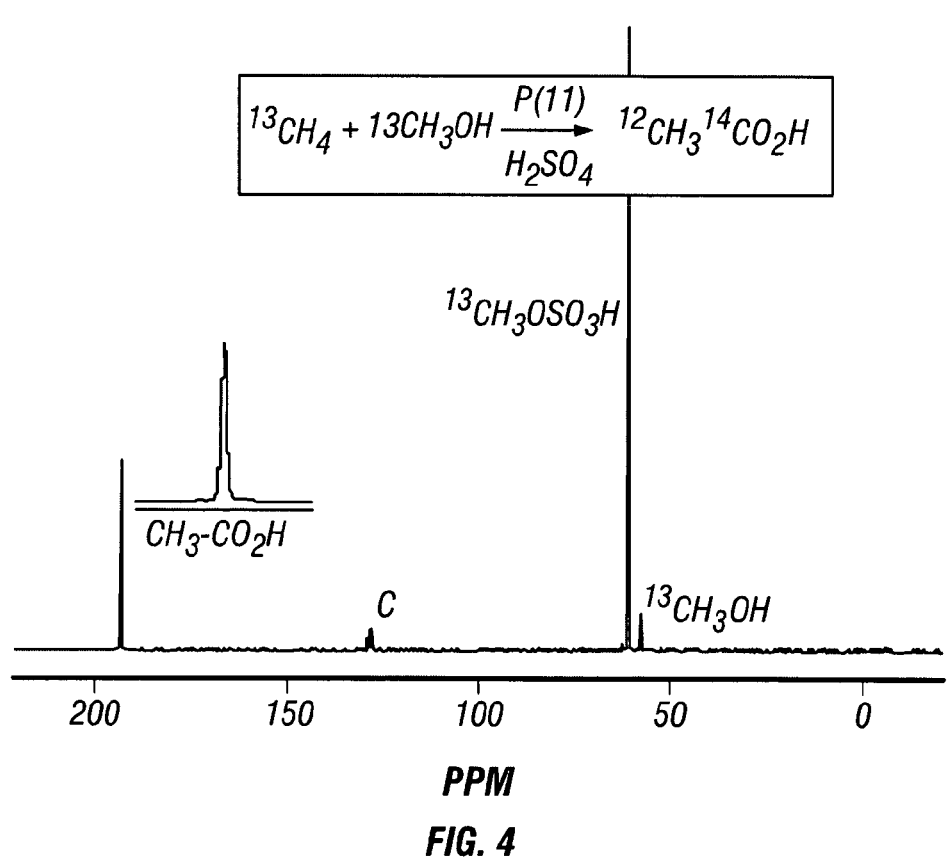
FIG. 4 is $^{13}C$ NMR of reaction mixture starting with $^{12}CH_4$ and $^{13}CH_3OH$.

To distinguish between pathways A, B and D, reactions starting with mixtures of $^{12}CH_4/^{13}CH_3OH$ and $^{13}CH_4/^{12}CH_3OH$ are separately examined (Periana et al., Science, 301, 814-18, 2003). Thus, when the reaction is carried out starting with the $^{12}CH_4/^{13}CH_3OH$ mixture and examined early in the reaction, pathway A should lead to $^{13}CH_3^{13}CO_2H$ and the diagnostic doublet pattern in the $^{13}C$ NMR spectrum due to $^{13}C$—$^{13}C$ coupling. In contrast, pathway B should lead to a singlet pattern resulting from formation of $^{12}CH_3^{13}CO_2H$ (or $^{13}CH_3^{12}CO_2H$) while pathway D should show no $^{13}C$ enriched acetic acid as only $^{12}CH_3^{12}CO_2H$ would form in this case. $^{13}C$ analysis of the crude reaction mixture after 15 minutes of reaction shows that the only $^{13}C$-enriched acetic acid produced is $^{12}CH_3^{13}CO_2H$ as shown by the large singlet resonance for the $^{13}CO_2H$ group at δ=192.4 and the complete absence of any resonance at δ=20.2 in FIG. 4. Consistent with this result, when the reaction is carried out with the $^{13}CH_4/^{12}CH_3OH$ mixture, the only $^{13}C$-enriched acetic acid produced is $^{13}CH_3^{12}CO_2H$. Thus, these experiments rule out pathways A and D and show that the C—C bond of acetic acid is assembled via pathway B from methane and methanol.

OTHER EMBODIMENTS

In certain embodiments, use of metal ligands in the reactions provided herein facilitates the dissolution of the metal. For example, in the case of Pt(bpym) $Cl_2$ system, 2,2'-bipyrimidine ligand facilitates the dissolution of Pt metal. Stable ligands that facilitate the oxidative dissolution of Pd by hot sulfuric acid can be used in the processes provided herein.

In certain embodiments, the $H_2SO_4$ oxidant can be replaced by $O_2$, $H_2SeO_4$, $TeO_3$, $H_2O_2$, trifluoroacetic, triflic acid or ionic liquids to achieve rapid oxidation of Pd metal.

In certain embodiments, the reaction can be carried out in presence of a Pt based catalyst. A platinum based catalyst, such as Pt(bpym)$Cl_2$, can be used for conversion of methane to acetic acid. Such reactions are carried out with an additional source of carbon such as, CO, $H_2CO$, $HCO_2H$ or methanol. In certain embodiments, triflic acid can be replaced for $H_2SO_4$ as an oxidant. In certain embodiments, gaseous CO is used as an additional source of carbon in the reaction. The reaction can be represented as follows:

Scheme II

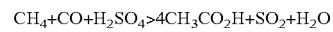

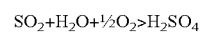

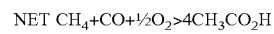

This reaction is less exothermic and easier to control and the process costs may be less. In certain embodiments, the CO is added as $HCO_2H$, or $CH_2O$ as these forms may be protected and less susceptible to over-oxidation to $CO_2$ than CO itself.

In certain embodiments, the Pt(bpym)$Cl_2$/$CH_4$/$H_2SO_4$ system to make acetic acid is used with Pd(II) or other platinum group metal catalysts. Exemplary catalysts include the catalysts that convert methanol to $CO_2$. Such catalysts are known in the art, and include platinum group metal/metal ions, Pt alloys, including, but not limited to Pt—Ru, Pt—Ir, Pt—Os and Pt—Mo.

The following examples are provided for illustrative purposes only and are not intended to limit the scope of the invention.

EXAMPLE 1

Conversion of Methane to Acetic Acid

Figure 1:
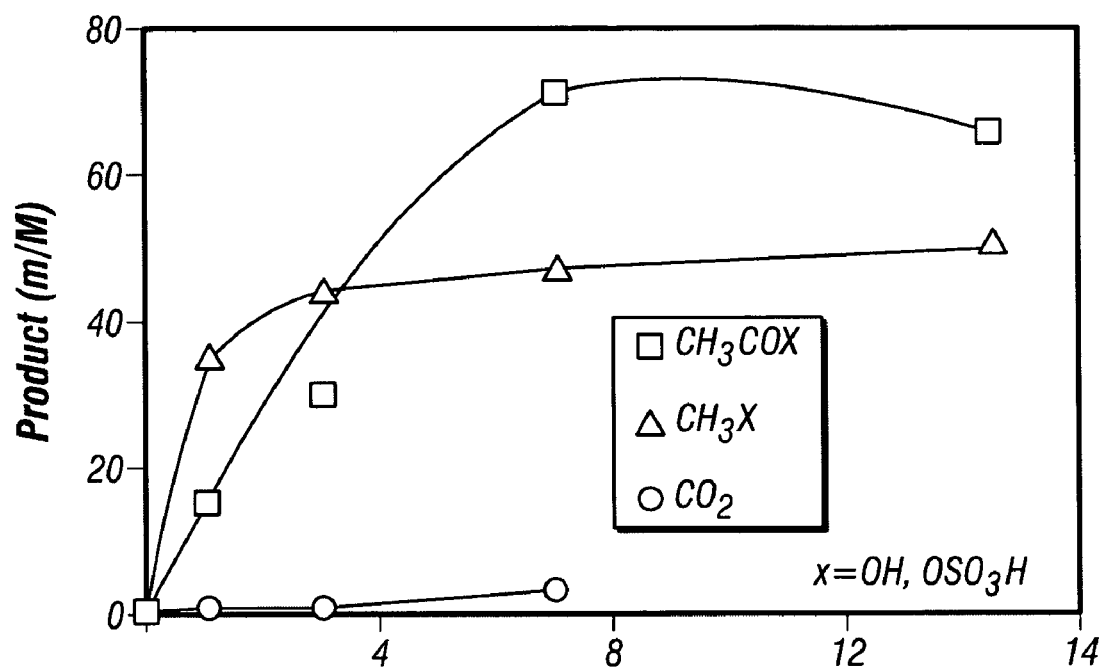
FIG. 1 illustrates time dependent formation of reaction products for production of Acetic Acid from Methane.

A 5 ml reactor was charged with 2 ml of 96% $H_2SO_4$, 20 mM $PdSO_4$, and 27.2 atm of $CH_4$. The reactor was heated to 180° C. with stirring. The reaction was cooled to room temperature. The liquid and gas phases were analyzed. FIG. 1 shows time dependent formation of reaction product in this reaction. As seen in FIG. 1, the selectivities for methanol and acetic acid were time dependent. The rate of formation of the products decreased with time and effectively stopped after 7 hours. Table 1 shows time-dependent selectivities for methanol and acetic acid formation:

TABLE 1

| Entry | Time (h) | TON | $CH_3OH$ (mM) | $CH_3CO_2H$ (mM) | $CO_2$ (mM) | Yield % | % Carbon selectivity $CH_3OH$ | $CH_3CO_2H$ | $CO_2$ | Additive |
|---|---|---|---|---|---|---|---|---|---|---|
| 1 | 1 | 5 | 35 | 15 | 0.01 | 4 (93) | 54 | 39 | 7 | — |
| 2 | 3 | 8 | 44 | 30 | 0.02 | 6 (91) | 39 | 52 | 9 | — |

TABLE 1-continued

| Entry | Time (h) | TON | CH$_3$OH (mM) | CH$_3$CO$_2$H (mM) | CO$_2$ (mM) | Yield % | % Carbon selectivity | | | Additive |
| --- | --- | --- | --- | --- | --- | --- | --- | --- | --- | --- |
| | | | | | | | CH$_3$OH | CH$_3$CO$_2$H | CO$_2$ | |
| 3 | 3 | 9 | 40 | 35 | 0.02 | 7 (92) | 33 | 59 | 8 | 10% O$_2$ |
| 4 | 7 | 18 | 38 | 82 | 0.05 | 12 (89) | 17 | 72 | 11 | — |
| 5 | 3 | <1 | 0 | 8 | 0.16 | ~1 | 0 | 17 | 83 | 5% CO |

TOF (Turnover frequency) ~$10^{-3}$ s$^{-1}$ after 1 hour at 180° C.; carbon mass balance >95%; TONs (Turnover numbers) were calculated as $\{(4\times[CH_3CO_2H]+([CH_3OH])/[PdSO_4]\}$. The % carbon yield of CH$_3$OH plus CH$_3$CO$_2$H is on the basis of added CH$_4$. The % carbon selectivity is relative to the total CH$_3$OH, CH$_3$CO$_2$H and CO$_2$ produced. Values in the parenthesis are the combined selectivity for CH$_3$OH and CH$_3$CO$_2$H. Dashed entries indicate no additives.

A number of embodiments have been described. Nevertheless, it will be understood that various modifications may be made without departing from the spirit and scope of the invention. Accordingly, other embodiments are within the scope of the following claims.

What is claimed is:

1. A process for converting methane to acetic acid comprising: reacting methane with a Pt, Pd, Rh, Ru, Os or Ir based catalyst and an oxidant in a reaction mixture; and separating acetic acid from the reaction mixture, wherein both carbon atoms of the acetic acid are derived from the methane.

2. The process of claim 1, wherein the catalyst is a Pd based catalyst.

3. The process of claim 1, wherein the catalyst is a Pd(II) catalyst.

4. The process of claim 1, wherein the catalyst is Pd(OAc)$_2$, PdSO$_4$, Pd(NO$_3$)$_2$ or PdCl$_2$.

5. The process of claim 1, wherein the catalyst is PdSO$_4$.

6. The process of claim 1, wherein the catalyst is a Pt based catalyst.

7. A process for converting methane to acetic acid comprising: reacting methane with a platinum group metal based catalyst, an oxidant and an additional source of carbon in a reaction mixture; and separating acetic acid from the reaction mixture, wherein the catalyst is Pt(bpym)Cl$_2$.

8. The process of claim 6, wherein the reaction mixture further comprises a second catalyst.

9. The process of claim 8, wherein the second catalyst is a Pd(II) catalyst.

10. The process of claim 9, wherein the second catalyst is PdSO$_4$.

11. The process of claim 7, wherein the additional source of carbon is CO, H$_2$CO, HCO$_2$H or methanol.

12. The process of claim 11, wherein the additional source of carbon includes CO.

13. The process of claim 1, wherein the oxidant is H$_2$SO$_4$, O$_2$, H$_2$SeO$_4$, TeO$_3$, H$_2$O$_2$, trifluoroacetic, triflic acid or an ionic liquid.

14. The process of claim 1, wherein the oxidant is H$_2$SO$_4$.

15. The process of claim 6, wherein the oxidant is H$_2$SO$_4$.

16. The process of claim 6, wherein the oxidant is triflic acid.

17. The process of claim 1, wherein the oxidant is H$_2$SO$_4$ and tie catalyst is PdSO$_4$.

18. The process of claim 1, wherein the reaction mixture is heated at 180° C.

19. The process of claim 1, wherein the conversion of methane to acetic acid occurs in a single step.

20. The process of claim 8, wherein the Pt based catalyst is Pt(bpym)Cl$_{12}$ and the second catalyst is Pd(II), a platinum group metal or a platinum alloy.

* * * * *

UNITED STATES PATENT AND TRADEMARK OFFICE
CERTIFICATE OF CORRECTION

PATENT NO.         : 7,368,598 B2                                      Page 1 of 1
APPLICATION NO.    : 11/186077
DATED              : May 6, 2008
INVENTOR(S)        : Roy A. Periana It is certified that error appears in the above-identified patent and that said Letters Patent is hereby corrected as shown below:

Title page, column 2, lines 7-8 (Other Publications) delete "Chem. Commun., pp. 1885-1886 (1998)," and insert -- Journal of catalysis 205(1):32-43, Jan. 2002. --;

Column 1, line 10, insert the following paragraph:
-- FEDERALLY SPONSORED RESEARCH OR DEVELOPMENT
This invention was made with government support under Contract No. CHE0328121 awarded by the National Science Foundation. The government has certain rights in the invention. --;

Column 6, line 33, (Claim 17) delete "tie" and insert -- the --;

Column 6, line 39, (Claim 20) delete "$Cl_{12}$" and insert -- $Cl_2$ --.

Signed and Sealed this

Twentieth Day of January, 2009

JON W. DUDAS
*Director of the United States Patent and Trademark Office*